United States Patent [19]

Gobert et al.

[11] Patent Number: 4,943,639

[45] Date of Patent: * Jul. 24, 1990

[54] (S)-ALPHA-ETHYL-2-OXO-1-PYRROLIDINEACETAMIDE

[75] Inventors: Jean Gobert, Brussels; Jean-Pierre Geerts, Leglise; Guy Bodson, Bellefontaine, all of Belgium

[73] Assignee: U C B Societe Anonyme, Brussels, Belgium

[*] Notice: The portion of the term of this patent subsequent to Jun. 6, 2006 has been disclaimed.

[21] Appl. No.: 311,631

[22] Filed: Feb. 16, 1989

Related U.S. Application Data

[62] Division of Ser. No. 25,277, Mar. 12, 1987, Pat. No. 4,837,223, which is a division of Ser. No. 733,790, May 24, 1985, Pat. No. 4,696,943.

[30] Foreign Application Priority Data

May 15, 1984 [GB] United Kingdom ................ 8412357

[51] Int. Cl.$^5$ ......................... C07D 207/277
[52] U.S. Cl. .................................... 548/550
[58] Field of Search ............... 548/546, 550; 514/424

Primary Examiner—David B. Springer
Attorney, Agent, or Firm—Wenderoth, Lind & Ponack

[57] ABSTRACT (S)-alpha-ethyl-2-oxo-1-pyrrolidineacetamide, its preparation and pharmaceutical compositions containing the same. It can be prepared either by reacting (S)-alpha-ethyl-2-oxo-1-pyrrolidineacetic acid successively with an alkyl haloformate and with ammonia, or, by cyclizing an (S)-2-amino-butanamide of the formula X—CH$_2$CH$_2$—Y—NHCH(C$_2$H$_5$)CONH$_2$ wherein Y is a —CH$_2$— radical when X represents a ZOOC— radical and Y is a —CO— radical when X represents a HalCH$_2$— radical, Z being a C$_1$–C$_4$ alkyl radical and Hal a halogen atom.

This laevorotatory enantiomer has been found to have significantly higher protective activity against hypoxia and ischemia than the corresponding racemate.

2 Claims, No Drawings

(S)-ALPHA-ETHYL-2-OXO-1-PYRROLIDINEACETAMIDE

This application is a division of application Ser. No. 025,277, filed Mar. 12, 1987, now U.S. Pat. No. 4,837,223, which application is, in turn, a division of application Ser. No. 733,790, filed May 24, 1985, now U.S. Pat. No. 4,696,943.

The present invention relates to the novel compound (S)-alpha-ethyl-2-oxo-1-pyrrolidineacetamide, as well as to processes for the preparation thereof. It also relates to pharmaceutical compositions containing the said compound.

British Pat. No. 1,309,692 describes the compound alpha-ethyl-2-oxo-1-pyrrolidineacetamide (melting point 122° C.) and states that the compounds of this type can be used for therapeutic purposes, for example for the treatment of motion sickness, hyperkinesia, hypertonia and epilepsy.

Moreover, it also mentions that these compounds can be applied in field of memory disorders in normal or pathological conditions.

It is also known that alpha-ethyl-2-oxo-1-pyrrolidineacetamide possesses a protective activity against aggressions of the central nervous system caused by hypoxias, cerebral ischemia, etc. (Pharmazie, 37/11, (1982), 753–765).

Continuing research work in this field, we have prepared and isolated the laevorotatory enantiomer of alpha-ethyl-2-oxo-1-pyrrolidineacetamide and have found that this compound differs in a completely unpredictable manner from the known racemic form, by (1) having a 10 times higher protective activity against hypoxia (antihypoxia) and
(2) having a 4 times higher protective activity against ischemia (antiischemia).

As a result of this unexpected combination of properties the laevorotatory enantiomer of alpha-ethyl-2-oxo-1-pyrrolidineacetamide is more suitable for the treatment and prevention of hypoxic and ischemic type aggressions of the central nervous system. The important contribution of the hypoxic phenomenon in certain pathological conditions of the central nervous system suggests that this compound has a therapeutic effect in the treatment of the consequences of cerebral vascular accidents and of cranial traumas, of the sequelae of the ageing process or of circulatory insufficiencies or the central nervous system resulting from cerebral-ischemic or hypoxic accidents occurring for example during birth. The compound may also be used in hypoxic-type diseases of other organs or tissues, such as the heart and kidneys.

Accordingly, the present invention relates to the laevorotatory enantiomer of alpha-ethyl-2-oxo-1-pyrrolidineacetamide which has the S absolute configuration, the said compound being substantially free from the dextrorotatory enantiomer which has the R absolute configuration.

(S)-alpha-ethyl-2-oxo-1-pyrrolidineacetamide according to the present invention cannot be obtained directly from the racemic form by separating the two enantiomers. It can be prepared by one or other of the following processes:

(a) reacting (S)-alpha-ethyl-2-oxo-1-pyrrolidineacetic acid successively with (1) an alkyl haloformate of the formula HalCOOZ in which Hal represents a halogen atom and Z an alkyl radical having 1 to 4 carbon atoms and with (2) ammonia. The alkyl haloformate is preferably ethyl chloroformate.

This reaction is generally carried out in dichloromethane at a temperature between −10° and −60° C.

The (S)-alpha-ethyl-2-oxo-1-pyrrolidineacetic acid, used in this reaction, can be obtained from the racemic (±)-alpha-ethyl-2-oxo-1-pyrrolidineacetic acid by chemical resolution in accordance with methods known per se, for example by forming a salt of this acid with an optically active base and isolating the salt formed with (S)-alpha-ethyl-2-oxo-1-pyrrolidineacetic acid by successive crystallizations an appropriate solvent (for example benzene).

By way of examples of optically active bases which can be used for this resolution there may be mentioned alkaloids such as brucine, quinine strychnine, quinidine and cinchonidine and amines such as alpha-methylbenzylamine and dehydroabietylamine (cf. S. H. WILEN et al., Tetrahedron, 33,(1977),2725–2736). Particularly favourable results are obtained by using alpha-methylbenzylamine and dehydroabietylamine.

The racemic (±)-alpha-ethyl-2-oxo-1-pyrrolidineacetic acid used as the starting material can be obtained by saponifying the corresponding alkyl esters, the synthesis of which has been described in British Pat. No. 1,309,692.

(b) cyclizing an (S)-2-amino-butanamide of the formula

$$X-CH_2CH_2-Y-NHCH(C_2H_5)CONH_2 \qquad (A)$$

in which

X represents a ZOOC— or HalCH$_2$— radical, Z being an alkyl radical having 1 to 4 carbon atoms, and Hal a halogen atom, preferably chlorine or bromine, and Y represents a —CH$_2$— or —CO— radical, with the proviso that Y is a —CH$_2$— radical when X represents a ZOOC— radical and Y is a —CO— radical when X represents a HalCH$_2$— radical. The cyclization of the (S)-2-amino-butanamide of formula A is carried out in an inert solvent, such as toluene or dichloromethane, at a temperature of from 0° C. to the boiling point of the solvent. This cyclization is advantageously carried out in the presence of a basic substance as a catalyst. This catalyst is preferably 2-hydroxypyridine when the compound of formula A is an ester (X=ZOOC—) and tetrabutylammonium bromide when the compound of formula A is a halide (X=HalCH$_2$—).

When X represents a ZOOC— radical and Y is a —CH$_2$— radical the compound of formula A is an alkyl (S)-4-[[1-(aminocarbonyl)propyl]amino]butyrate of the formula ZOOCCH$_2$CH$_2$CH$_2$NHCH(C$_2$H$_5$)CONH$_2$, in which Z has the meaning given above. The latter can be prepared by condensing (S)-2-amino-butanamide with an alkyl 4-halobutyrate of the formula ZOOCCH$_2$CH$_2$CH$_2$Hal, in which Z has the meaning given above and Hal is a halogen atom.

When X represents a HalCH$_2$— radical and Y is thus a —CO— radical, the compound of formula A is (S)-N-[1-(aminocarbonyl)propyl]-4-halobutanamide of the formula HalCH$_2$CH$_2$CH$_2$CONHCH(C$_2$H$_5$)CONH$_2$, in which Hal has the meaning given above. This latter compound can be prepared by condensing (S)-2-amino-butanamide with a 4-halobutyryl halide of the formula HalCH$_2$CH$_2$CH$_2$COHal, in which Hal is a halogen atom.

The reaction between the (S)-2-amino-butanamide on the one hand and the alkyl 4-halobutyrate or 4-halobutyryl halide on the other hand, is generally carried out in an inert solvent, such as benzene, toluene, dichloromethane or acetonitrile, at a temperature of from $-5°$ to $+100°$ C. and in the presence of an acid acceptor such as a tertiary organic base (for example triethylamine) or an inorganic base (for example potassium carbonate or hydroxide or sodium carbonate or hydroxide).

When X represents a $HalCH_2-$ radical and Y a $-CO-$ radical, it is not absolutely necessary to isolate the compound of formula A obtained from the starting materials mentioned above. In fact, the compound of formula A, obtained in situ, can be cyclized directly to the (S)-alphaethyl-2-oxo-1-pyrrolidineacetamide according to the present invention (see Example 4 below).

The (S)-2-amino-butanamide used as starting material can be obtained from (S)-2-amino-butyric acid by ammonolysis of the corresponding methyl ester in accordance with the method described by K. FOLKERS et in J.Med.Chem.14,(6),(1971),484–487.

The following examples are given for the purpose of illustration only

In these examples, the optical purity of the compounds obtained was verified by calorimetric determination of the differential enthalpies (C. FOUQUEY and J. JACQUES, Tetrahedron,23,(1967),4009–19).

EXAMPLE 1

(a) Preparation of the (R)-alpha-methyl-benzylamine salt of (S)-alpha-ethyl-2-oxo-1-pyrrolidineacetic acid 8.7 kg (50.8 moles) of racemic ($\pm$)-alpha-ethyl-2-oxo-1-pyrrolidineacetic acid are suspended in 21.5 liters of anhydrous benzene in a 50 liter reactor. To this suspension is added gradually a solution containing 3.08 kg (25.45 moles) of (R)-(+)-alpha-methyl-benzylamine and 2.575 kg (25.49 moles) of triethylamine in 2.4 liters of anhydrous benzene. This mixture is then heated to reflux temperature until complete dissolution It is then cooled and allowed to crystallize for a few hours. 5.73 kg of the (R)-alpha-methyl-benzylamine salt of (S)-alpha-ethyl-2-oxo-1-pyrrolidineacetic acid are thus obtained.

Melting point: 148°–151° C. Yield: 77.1%.

This salt may be purified by heating under reflux in 48.3 liters of benzene for 4 hours. The mixture is cooled and filtered to obtain 5.040 kg of the desired salt. Melting point: 152°–153.5° C. Yield: 67.85%.

(b) Preparation of (S)-alpha-ethyl-2-oxo-1-pyrrolidineacetic acid 5.04 kg of the salt obtained in (a) above are dissolved in 9 liters of water. 710 g of a 30% sodium hydroxide solution are added slowly so that the pH of the solution reaches 12.6 and the temperature does not exceed 25° C. The solution is stirred for a further 20 minutes and the alpha-methylbenzylamine liberated is extracted repeatedly with a total volume of 18 liters of benzene.

The aqueous phase is then acidified to a pH of 1.1 by adding 3.2 liters of 6N hydrochloric acid. The precipitate formed is filtered off, washed with water and dried.

The filtrate is extracted repeatedly with a total volume of 50 liters of dichloromethane. The organic phase is dried over sodium sulfate and filtered and evaporated to dryness under reduced pressure.

The residue obtained after the evaporation and the precipitate isolate previously, are dissolved together in 14 liters of hot dichloromethane. The dichloromethane is distilled and replaced at the distillation rate, by 14 liters of toluene from which the product crystallizes.

The mixture is cooled to ambient temperature and the crystals are filtered off to obtain 2.78 kg of (S)-alpha-ethyl-2-oxo-1-pyrrolidineacetic acid.

Melting point: 125.9° C. $[alpha]_D^{20} = -26.4°$ (c=1, acetone). Yield: 94.5%.

(c) Preparation of (S)-alpha-ethyl-2-oxo-1-pyrrolidineacetamide 34.2 g (0.2 mole) of (S)-alpha-ethyl-2-oxo-1-pyrrolidineacetic acid are suspended in 225 ml of dichloromethane cooled to $-30°$ C. 24.3 g (0.24 mole) of triethylamine are added dropwise over 15 minutes. The reaction mixture is then cooled to $-40°$ C. and 24.3 g (0.224 mole) of ethyl chloroformate are added over 12 minutes. Thereafter, a stream of ammonia is passed through the mixture for 4½ hours. The reaction mixture is then allowed to return to ambient temperature and the ammonium salts formed are removed by filtration and washed with dichloromethane. The solvent is distilled off under reduced pressure. The solid residue thus obtained is dispersed in 55 ml toluene and the dispersion is stirred for 30 minutes and then filtered. The product is recrystallized from 280 ml of ethyl acetate in the presence of 9 g of 0,4 nm molecular sieve in powder form.

24.6 g of (S)-alpha-ethyl-2-oxo-1-pyrrolidineacetamide are obtained.

Melting point: 115°–118° C. $[alpha]_D^{25} = -89.7°$ (c=1, acetone). Yield: 72.3%.

Analysis for $C_8H_{14}N_2O_2$ in % calculated: C 56.45. H 8.29. N 16.46. found: 56.71. 8.22. 16.48.

The racemic ($\pm$)-alpha-ethyl-2-oxo-1-pyrrolidineacetic acid used in this synthesis has been prepared in the manner described below.

A solution containing 788 g (19.7 moles) of sodium hydroxide in 4.35 liters of water is introduced over 2 hours into a 20 liter flask containing 3.65 kg (18.34 moles) of ethyl ($\pm$)-alpha-ethyl-2-oxo-1-pyrrolidineacetate at a temperature not exceeding 60° C. When this addition is complete, the temperature of the mixture is raised to 80° C. and the alcohol formed is distilled off until the temperature of the reaction mixture reaches 100° C.

The reaction mixture is then cooled to 0° C. and 1.66 liter (19.8 moles) of 12N hydrochloric acid is added over two and a half hours. The precipitate formed is filtered off, washed with 2 liters of toluene and recrystallized from isopropyl alcohol. 2.447 kg of racemic ($\pm$)-alpha-ethyl-2-oxo-1-pyrrolidineacetic acid, melting at 155°–156° C., are thus obtained. Yield: 78%.

Analysis for $C_8H_{13}NO_3$, in % calculated: C 56.12. H 7.65. N 8.18. found: 55.82. 8.10. 7.97.

EXAMPLE 2

(a) Preparation of ethyl (S)-4-[[1-(aminocarbonyl)propyl]amino]butyrate 143.6 ml (1.035 mole) of triethylamine are added to a suspension of 47.75 g (0.345 mole) of (S)-2-aminobutanamide hydrochloride ($[alpha]_D^{25}$: +26.1°; c=1, methanol) in 400 ml of toluene. The mixture is heated to 80° and 67.2 g (0.345 mole) of ethyl 4-bromobutyrate are introduced dropwise.

The reaction mixture is maintained at 80° C. for 10 hours and then filtered hot to remove the triethylamine salts. The filtrate is then evaporated under reduced pressure and 59 g of an oily residue consisting essentially of the monoalkylation product but containing also a small amount of dialkylated derivative are obtained.

The product obtained in the crude state has been used as such, without additional purification, in the preparation of (S)-alpha-ethyl-2-oxo-1-pyrrolidineacetamide by cyclization.

(b) Preparation of
(S)-alpha-ethyl-2-oxo-1-pyrrolidineacetamide 54 g of the crude product obtained in a) above are dissolved in 125 ml of toluene in the presence of 2 g of 2-hydroxypyridine. The mixture is heated at 110° C. for 12 hours.

The insoluble matter is filtered off hot and the filtrate is then evaporated under reduced pressure.

The residue is purified by chromatography on a column of 1.1 kg of silica (column diameter: 5 cm; eluent: a mixture of ethyl acetate, methanok and concentrated ammonia solution in a proportion by volume of 85:12:3).

The product isolated is recrystallized from 50 ml of ethyl acetate to obtain 17.5 g of (S)-alpha-ethyl-2-oxo-1-pyrrolidineacetamide.

Melting point: 117° C. $[alpha]_D^{25}$: $-90.0°$ (c=1, acetone). Yield: 41%.

EXAMPLE 3

(a) Preparation of
(S)-N-[1(aminocarbonyl)propyl]-4-chlorobutanamide 345.6 g (2.5 moles) of ground potassium carbonate are mixed with 138.5 g (1 mole) of (S)-2-amino-butanamide hydrochloride in 2.5 liters of acetonitrile. The reaction mixture is cooled to 0° C. and a solution of 129.2 g (1.2 mole) of 4-chlorobutyryl chloride in 500 ml of acetonitrile is introduced dropwise. After the addition, the reaction mixture is allowed to return to ambient temperature; the insoluble matter is filtered off and the filtrate evaporated under reduced pressure. The crude residue obtained is stirred in 1.2 liter of anhydrous ether for 30 minutes at a temperature between 5° and 10° C. The precipitate is filtered off, washed twice with 225 ml of ether and dried in vacuo to obtain 162.7 g of (S)-N-[1-(aminocarbonyl)propy]-4-chlorobutanamide.

Melting point: 118°–123° C. $[alpha]_D^{25}$: $-18°$ (c=1, methanol). Yield: 78.7%.

The crude product thus obtained is very suitable for the cyclization stage which follows. It can however be purified by stirring for one hour in anhydrous ethyl acetate.

Melting point: 120°–122° C. $[alpha]_D^{25}$: $-22.2°$ (c=1, methanol).

(b) Preparation of
(S)-alpha-ethyl-2-oxo-1-pyrrolidineacetamide 6.2 g (0.03 mole) of (S)-N-[1(aminocarbonyl)propyl]-4-chlorobutamine and 0.484 g (0.0015 mole) of tetrabutylammonium bromide are mixed in 45 ml of dichloromethane at 0° C. under a nitrogen atmosphere. 2.02 g (0.036 mole) of potassium hydroxide powder are added over 30 minutes, at such a rate that the temperature of the reaction mixture does not exceed +2° C. The mixture is then stirred for one hour, after which a further 0.1 g (0.0018 mole) of ground potassium hydroxide is added and stirring continued for 30 minutes at 0° C. The mixture is allowed to return to ambient temperature. The insoluble matter is filtered off and the filtrate is concentrated under reduced pressure. The residue obtained is recrystallized from 40 ml of ethyl acetate in the presence of 1.9 g of 0,4 nm molecular sieve. The latter is removed by hot filtration to give 3.10 g of (S)-alphaethyl-2-oxo-1-pyrrolidineacetamide.

Melting point: 116.7° C. $[alpha]_D^{25}$: $-90.1°$ (c=1, acetone). Yield: 60.7%.

EXAMPLE 4

Preparation of
(S)-alpha-ethyl-2-oxo-1-pyrrolidineacetamide

This example illustrates a variant of the process of Example 3, in which the intermediate 4-chlorobutanamide obtained in situ is not isolated. 84 g of anhydrous sodium sulfate are added to a suspension of 69.25 g (0.5 mole) of (S)-2-amino-butanamide hydrochloride in 600 ml of dichloromethane at ambient temperature. The mixture is cooled to 0° C. and 115 g of ground potassium hydroxide are added, followed by 8.1 g (0.025 mole) of tetrabutylammonium bromide dissolved in 100 ml of dichloromethane. A solution of 77.5 g of 4-chlorobutyryl chloride in 100 ml of dichloromethana is added dropwise at 0° C., wih vigorous stirring. After 5 hours' reaction, a further 29 g of ground potassium hydroxide are added. Two hours later, the reaction mixture is filtered over Hyflo-cel and the filtrate evaporated under reduced pressure. The residue (93.5 g) is dispersed in 130 ml of hot toluene for 45 minutes. The resultant mixture is filtered and the filtrate evaporated under reduced pressure. The residue (71.3 g) is dissolved hot in 380 ml of ethyl acetate to which 23 g of 0,4 nm molecular sieve in powder form are added. This mixture is heated to reflux temperature and filtered hot. After cooling the filtrate, the desired product crystallizes to give 63 g of (S)-alpha-ethyl-2-oxo-1-pyrrolidineacetamide.

Melting point: 117° C. $[alpha]_D^{25}$: $-91.3°$ (c=1, acetone). Yield: 74.1%.

Pharmcological tests

Racemic alpha-ethyl-2-oxo-1-pyrrolidineacetamide (compound A) and (S)-alpha-ethyl-2-oxo-1-pyrrolidineacetamide (compound B) of the present invention were subjected to pharmcological tests.

I. Protection against hypoxia (mouse)

a. Principle (C. GIURGEA and F. MOURAVIEFF-LESUISSE; Proc.Xth Intern. Congr. of the Coll. Intern. Neuro-psych.- Pergamon Press, Oxford and New York, 1978, p.1623-1631).

The principle of this test lies in measuring the possibilities of survival of the organism subjected to an atmosphere in which the oxygen level is progressively decreased. Due to the particular sensitivity of the nervous system to this type of aggression, the results obtained in this test can be interpreted as a measure of the resistance of the central nervous system. Compounds which increase the resistance of the animals to this stress are suitable for the treatment and prevention of hypoxic type aggressions of the central nervous system.

b. Method

The apparatus consists of an airtight transparent cage 37 cm high, 39 cm deep and 97 cm wide. This 140 liter cage is provided with 60 transparent compartments each 6×10×10 cm, making it possible to separately accomodate 60 mice.

A fan ensures circulation of the atmosphere between the compartments through a grid floor. The cage is equipped with a device for introducing nitrogen at a constant flow rate, and with an orifice communicating with the ambient atmosphere. Male mice (NMRI strain) weighing 20 to 22 g, are kept fasting as from the day before the test. The experiment is effected on the following day, simultaneously on 3 groups of 20 mice; a control group is given water (25 ml/kg) orally, and the other two groups are each given orally a compound to be tested.

25 minutes after the administration, the animals are distributed at random amongst the compartments so that none of the three groups is concentrated in a preferred area of the cage.

30 minutes after administration, the cage is closed and nitrogen is admitted into it at a constant flow rate (7.75 liters of technical grade nitrogen per minute) for about 37 minutes, at which stage the atmosphere contains 3.7% oxygen.

The cage is left closed until the critical moment where no more than 3 survivors are observed among the 20 control animals. At that moment, the cage is opened and atmospheric air admitted into it. A few moments later the survivors in each group of animals are counted.

For each dose of compound to be tested, the experiments are repeated once or twice, and the results pooled to obtain a minimum of 40 (or 60 animals treated per dose and 40 (or 60) corresponding control animals. For each dose of compound tested, the number of surviving animals among those treated with the compound is compared with the number of surviving animals among the control animals. The difference between these numbers expresses the protective activity of the compound against hypoxia caused by oxygen deprivation. The statistical significance (P) of this difference is evaluated by the Fischer-Yates test.

c. Results

Table I below gives the results obtained for increasing doses of compounds A and B.

TABLE I

| Compound tested | Oral dose in mmol/kg | Number of surviving animals | | P |
| --- | --- | --- | --- | --- |
| | | control | treated | |
| A | 0.032 | 12/60 | 16/60 | NS |
| | 0.1 | 8/60 | 7/60 | NS |
| | 0.16 | 12/60 | 12/60 | NS |
| | 0.32 | 10/60 | 30/60 | <0.001 |
| B | 0.016 | 5/40 | 11/40 | NS |
| | 0.032 | 8/40 | 17/40 | <0.6 |
| | 0.1 | 6/40 | 19/40 | <0.005 |
| | 0.16 | 6/40 | 19/40 | <0.005 |
| | 0.32 | 5/40 | 17/40 | <0.01 |

NS = statistically non-significant.

d. Conclusions

In this test, the laevorotatory enantiomer of the invention (compound B) increases the survival of the animals deprived of oxygen when administered at doses from 0.032 mmol/kg upwards. The racemate (compound A) exerts a similar activity only from 0.32 mmol/kg upwards (1st effective dose). Thus, the laevorotatory enantiomer of the present invention is 10 times more active than the corresponding racemate.

II. Protection against cerebral ischemia (rats)

a. Principle (C. GIURGEA and F. MOURAVIEFF-LESUISSE; see above under Ia.) Electroencephalographic controls have shown that the ligature of the 2 common carotids in the rat causes a true cerebral ischemia: the electroencephalogram trace flattens and even becomes isoelectric (electric silence).

b. Method

Male Wistar rats weighing between 250 and 350 g are anesthetized with pentobarbital administered intraperitoneally at a dose of 50 mg/kg (0.5 ml/100 g).

Immediately after the anesthesia, the animals are administered intraperitoneally with an amount of 0.5 ml/100 g, either the compound to be tested dissolved in an isotonic sodium chloride solution (treated animals), or only an isotonic sodium chloide solution or placebo (control animals). About 20 minutes later, the 2 common carotids are exposed and about 10 minutes later ligatured simultaneously. This operation is effected simultaneously on the control animals and the treated animals.

An hour after administration of the compound to be tested or of the placebo, there is again administered intraperitoneally the same dose of either the compound to be tested (to the treated animals) or the place (to the control animals).

5 hours after the first administration, there is administered for the third time the same dose of either the compound to be tested (to the surviving treated animals) or the placebo (to the surviving control animals).

24 hours after the first administration the efficacy of the ligature is verified in all animals, under pentobarbital anesthesia, by section or the carotids downstream of the ligature. The number of surviving animals is recorded among both the treated animals and the control animals. For each dose of compound tested, the number of surviving animals among those treated with the compound is compared with the number of surviving animals among the control animals. The difference expresses the protective activity of the compound against the lethality induced by the simultaneous ligature of the 2 carotids. The statistical significance (P) of this difference is evaluated by the Brandt-Snedecor test.

c. Results

Table II below gives the results obtained for increasing doses of compounds A and B.

TABLE II

| Compound tested | Intraperitoneal dose in mmol/kg | Number of surviving animals | | P |
| --- | --- | --- | --- | --- |
| | | control | treated | |
| A | 0.32 | 6/29 | 8/29 | NS |
| | 0.64 | 11/30 | 21/30 | 0.01 |
| B | 0.1 | 9/29 | 14/29 | NS |
| | 0.16 | 6/29 | 14/30 | 0.05 |
| | 0.32 | 8/30 | 19/29 | 0.01 |

NS = non-significant difference.

d. Conclusions

Table II shows that the racemate (compound A) is only active from a dose of 0.64 mmol/kg upwards. In contrast, the laevorotatory enantiomer of the invention (compound B) protects the animals, from 0.16 mmol/kg upwards, against the lethality induced by the simultaneous ligature of the two carotids and thus proves to be 4 times more active than the racemate.

III. Toxicity

Table III below gives, for compounds A and B, the $LD_{50}$, in mg/kg, determined on the male mouse and the male rat after intravenous administration:

TABLE III

| Compound tested | $LD_{50}$ in mg/kg | |
| --- | --- | --- |
| | mouse | rat |
| A | 1790 | 1500 |
| B | 1081 | 1038 |

As can be seen from this table the laevorotatory enantiomer of the invention (compound B) has, like the racemate (compound A), very low toxicity and the toxic dose is well above the active dose.

The compound of the present invention can be administered either orally in the form of solid or liquid compositions for example, in the form of tablets, pills, degrees, gelatine capsules, solutions or syrups, or parenterally in the form of injectable solutions or suspensions. Pharmaceutical forms such as solutions or tablets are prepared according to conventional pharmaceutical methods. The compound of the invention may be mixed with a solid or liquid non-toxic pharmaceutically acceptable carrier and optionally with a dispersant, a stabilizer and where necessary, colorants and sweeteners.

Similarly the solid or liquid pharmaceutical carriers used in these compositions are well known.

Solid pharmaceutical excipients for the preparation of tablets or capsules include, for example, starch, talc, calcium carbonate, lactose, sucrose and magnesium stearate.

The percentage of active product in the pharmaceutical compositions can vary within very wide limits depending upon the mode of administration and the condition of the patient. The human posology can vary between 250 mg and 3 g per day.

There is given below a non-limiting example of a composition containing the compound of the invention i.e. a 100 mg gelatine capsule for oral administration:

| compound B | 100 mg |
| --- | --- |
| avicel (microcrystalline cellulose) | 217 mg |
| Mg stearate | 5 mg |

We claim:
1. (S)-alpha-ethyl-2-oxo-1-pyrrolidineacetamide substantially free of (R)-alpha-ethyl-2-oxo-1-pyrrolidineacetamide.
2. (S)-alpha-ethyl-2-oxo-1-pyrrolidineacetamide substantially free of (R)-alpha-ethyl-2-oxo-1-pyrrolidineacetamide, prepared by the process which comprises reacting (S)-alpha-ethyl-2-oxo-1-pyrrolidineacetic acid successively with (1) an alkyl haloformate of the formula HalCOOZ in which Hal represents a halogen atom and Z represents an alkyl radical having 1 to 4 carbon atoms, and with (2) ammonia.

* * * * *

UNITED STATES PATENT AND TRADEMARK OFFICE

(12)   CERTIFICATE EXTENDING PATENT TERM
       UNDER 35 U.S.C. § 156

(68) PATENT NO.      : 4,943,639

(45) ISSUED          : July 24, 1990

(75) INVENTOR        : Jean Gobert, et al.

(73) PATENT OWNER    : UCB SOCIETE ANONYME

(95) PRODUCT         : KEPPRA® (levetiracetam)

This is to certify that an application under 35 U.S.C. § 156 has been filed in the United States Patent and Trademark Office, requesting extension of the term of U.S. Patent No. 4,943,639 based upon the regulatory review of the product KEPPRA (levetiracetam) by the Food and Drug Administration. Since it appears that the requirements of the law have been met, this certificate extends the term of the patent for the period of

(94)                   1,157 days from June 6, 2006, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 7th day of January 2004.

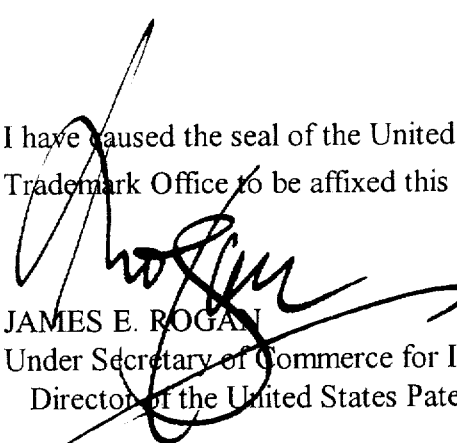

JAMES E. ROGAN
Under Secretary of Commerce for Intellectual Property and
Director of the United States Patent and Trademark Office

UNITED STATES PATENT AND TRADEMARK OFFICE
CERTIFICATE OF CORRECTION

PATENT NO. : 4,943,639
DATED : July 24, 1990
INVENTOR(S) : Jean Gobert et al.

It is certified that error appears in the above-identified patent and that said Letters Patent is hereby corrected as shown below:

<u>Title page,</u>
Item [*] Notice, "The portion of this patent subsequent to June 6, 2006 has been disclaimed." should read -- This patent is subject to a terminal disclaimer. --.
Item [86], 35 U.S.C § 156, "from June 6, 2006," should read -- from May 14, 2005, --.

Signed and Sealed this

Fourteenth Day of June, 2005

JON W. DUDAS
*Director of the United States Patent and Trademark Office*

Disclaimer 4,943,639—Jean Gobert, Brussels; Jean-Pierre Geerts, Leglise; Guy Bodson, Bellefontaine, all of Belgium.(S)-ALPHA-ETHYL-2-OXO-1-PYR- ROLIDINEACETAMIDE. Patent dated Jul. 24, 1990. Disclaimer filed Mar. 22, 2005, by the Assignee, U C B Societe Anonyme.

The term of this patent which would extend beyond the expiration date of Pat. Nos. 4,837,223 and 4,696,943.

*(Official Gazette March 18, 2008)*